United States Patent
Kirchner

(10) Patent No.: US 7,512,510 B2
(45) Date of Patent: Mar. 31, 2009

(54) DEVICE FOR THE PREPARATION EXECUTION AND EVALUATION OF A NON-DESTRUCTIVE ANALYSIS

(75) Inventor: Bernd Kirchner, Erftstadt (DE)

(73) Assignee: GR Inspection Technologies GmbH (DE)

( * ) Notice: Subject to any disclaimer, the term of this patent is extended or adjusted under 35 U.S.C. 154(b) by 0 days.

(21) Appl. No.: 10/582,020

(22) PCT Filed: Nov. 19, 2004

(86) PCT No.: PCT/DE2004/002547

§ 371 (c)(1), (2), (4) Date: Jun. 8, 2006

(87) PCT Pub. No.: WO2005/057203

PCT Pub. Date: Jun. 23, 2005

(65) Prior Publication Data

US 2007/0112539 A1    May 17, 2007

(30) Foreign Application Priority Data

Dec. 8, 2003   (DE) ............................... 103 57 595

(51) Int. Cl.
*G01R 31/00* (2006.01)
*G06F 19/00* (2006.01)

(52) U.S. Cl. ..................... 702/121; 702/120
(58) Field of Classification Search ............. 702/120, 702/121, 122, 182, 34, 35; 73/656, 657, 73/602; 356/237.2, 369
See application file for complete search history.

(56) References Cited

U.S. PATENT DOCUMENTS

| | | | | |
|---|---|---|---|---|
| 6,301,512 B1 * | 10/2001 | Motzer | ......................... | 700/90 |
| 6,301,967 B1 * | 10/2001 | Donskoy et al. | .............. | 73/579 |
| 6,606,153 B2 * | 8/2003 | Marxer et al. | ............ | 356/237.3 |

OTHER PUBLICATIONS

Deutsch et al; "Ultraschallpruefung: Grundlagen und industrielle anwendungen"; 1997, Springer Verlag, Berlin Heidelberg, XP002322577 ISBN: 3-540-62072-9; pp. 62-68;214-217;336-340; Figures 3.16, 3.29, 3.30B, 3.34; Tables 8.1 to 8.3.*

* cited by examiner

*Primary Examiner*—Bryan Bui
(74) *Attorney, Agent, or Firm*—Cantor Colburn LLP

(57) ABSTRACT

The invention relates to a device (10), for the preparation, execution and evaluation of a non-destructive analysis with one or more suitable analysis devices (20) of any type. The device (10) includes an input device (12), an output device (14), a data store, a data processing unit (16), an interface (18) for connection of the analysis device (14), by means of which data may be transmitted in both directions and a standardised data processing programme. It is possible to generate an analysis flow scheme, by means of the data processing programme, whereby an analysis object (26) can be defined, various analysis regions (28) of the analysis object (26) can be determined, a particular analysis device (20) can be selected, analytically-relevant parameters can be selected and determined for the selected analytical device (20), the type of visualisation and the analysis of the measured analytical values can be determined and the obtained analytical results can be archived and stored.

11 Claims, 2 Drawing Sheets

DEVICE FOR THE PREPARATION EXECUTION AND EVALUATION OF A NON-DESTRUCTIVE ANALYSIS

TECHNICAL FIELD OF INVENTION

The present invention pertains to an apparatus for preparing, performing and evaluating a non-destructive inspection. The invention is for example suited for ultrasonic, X-ray or thermography inspection methods.

BRIEF DESCRIPTION OF RELATED ART

Non-destructive material inspection serves to detect defects (such as cracks, bubbles, pores, inclusions, and so on), to determine coatings, inner walls and wall thicknesses and to control imposed material properties without compromising the usability of the component. This makes complete inspection of individual parts possible, thus allowing for more reliable evidence as compared to sample inspection. In ultrasonic inspection, ultrasonic waves propagate in a straight line in the frequency range of from about 100 kHz to 25 MHz in solid bodies and are reflected at the interfaces. In the transmission technique, the test piece is interposed between the sound transmitter and the receiver. The sound waves traversing the workpiece are reconverted to electric vibrations and displayed by the receiver. It is not possible to determine the depth of the defect with this technique. In the pulse-echo method, the sound probe is used as both transmitter and receiver whereby short sound pulses are sent into the workpiece and reconverted to a receiver pulse by the same sound probe after complete or partial reflection. Transmitter pulse, backwall echo and defect echo are recorded electronically and depth can be determined over the respective time of flight. The use of angle beam probes with an insonification angle of between 35° and 80° permits testing of weld seams in particular since the coupling may occur outside of the rough seam surface. Locating weld flaws is possible (also see J. Krautkrämer, H. Krautkrämer, Werkstoffprüfung mit Ultraschall (*Ultrasonic Testing of Materials*), Springerverlag; Dubbel, Taschenbuch für den Maschinenbau (*Engineer's Pocketbook*).

Beside the various fundamental possibilities of ultrasonic inspection, these possibilities may also for example be subdivided into ultrasonic, eddy current, surface hardness inspection, and so on.

If now a complex test object is to be inspected, the first thing to determine with regard to the results one would like to obtain is which method should be used to inspect which regions of the test object. If a pipeline for example is to be inspected, various regions can only be inspected with certain test methods whilst other regions in turn require other test methods. Testing the wall thickness of the pipeline is for example different from testing the weld seams or the head pieces.

Once it has been determined which test methods are appropriate, or where which test method is to be utilized, the next step usually is to select and set the appropriate test instruments for the respective one of the appropriate test method. Further, the decision is taken whether additional instruments (scanners, moving instruments for guiding the probes and instruments, and so on) might possibly be utilized. If this is the case, these are also selected and set. It must further be decided how the test values obtained are to be represented and visualized. The representation and visualization may occur during testing already or thereafter, the same also applying to the subsequent work step consisting in valuing and evaluating the test values, which may also occur online or offline. Finally, archiving and documentation are necessary in most cases.

Accordingly, planning and performing an ultrasonic inspection is a very complex procedure requiring on the one hand a very experienced planner and on the other side also comprising multiple sources of error. In prior art, these difficulties are substantially solved by three systems, namely by self-sufficient (manual) test instruments, by PC-based test instruments and PC-evaluation, documentation and administration programs, with these systems being often used in combination.

The self-sufficient handheld test instrument is e.g. available for ultrasonic, eddy current, surface hardness tests and so on. It contains a user interface and functions for administrating its setting parameters and the test results produced therewith. Additional interfaces for importing and exporting data are also provided. This test instrument however may only be used in its determined generic range of functions.

PC-based test instruments, meaning computer-assisted test instruments, substantially have the same range of functions as the self-sufficient handheld instrument. Due to a PC-based operating system (such as Windows), they have a clearer graphical user interface and use the scope of function of the operating system with regard to hardware interfaces (e.g. USB, LAN, hard disk, and so on) to full capacity. Since for ultrasonic inspection a hardware is to be addressed that is designed for personal computers, Windows application (*.exe) is here committed on hardware and, as a result thereof, on inspection.

PC-evaluation, documentation and administration programs are mostly passive in nature, i.e., they are generally used offline or they establish a point-to-point connection with known connected test instruments only.

As a result, combined inspection methods such as weld seam testing consisting of an ultrasonic and a hardness inspection cannot for example be performed using a common user interface. Moreover, there is no superior abstract administration of a test that is independent of the instruments to be utilized.

In addition thereto, operation of the various instruments or groups of instruments differs so that the test operator needs to be acquainted with all the instruments.

BRIEF SUMMARY OF THE INVENTION

The invention provides an apparatus for preparing, performing and evaluating a non-destructive inspection that is connectable with any test instrument. It is intended that a superior abstract inspection planning that integrates the various test instruments, evaluation and analysis methods be carried out. The apparatus is intended to be easy to operate and manufacturable at a low cost.

In accordance with the invention, an apparatus is provided for preparing, performing and evaluating a non-destructive inspection, said apparatus having one or more discretionary suitable test instruments and comprising:
 a) an input device,
 b) an output device
 c) a data store,
 d) a data processing unit,
 e) an interface for connecting a respective one of the test instruments through which data are adapted to be transmitted in both directions,
 f) a standardized data processing program for
  defining a test object by data input or selecting it from the data store, determining various test regions of a test object,
selecting at least one determined test instrument from a group of test instruments and associating it with a respective one of the test regions, with all relevant properties of the test instrument being stored in the data store,
carrying out test-relevant settings for the selected instrument,
selecting the manner of visualizing and evaluating measured test values,
archiving and storing test results obtained,
establishing a test scheme, with all the predetermined settings being transferred to the respective test instrument upon connection thereof so that it is preset for inspection.

The apparatus of the invention accordingly is a superior instrument for combining and controlling specific test instruments, and for administrating test functions based on an inspection plan.

In accordance with the invention, a commercially available PC, a commercially available notebook or a PDA handheld computer can be utilized as an apparatus, using corresponding software. Any operating system, in particular a window-oriented operating system, is suited for this purpose.

With a test object, for example a pipeline, it is possible to first associate certain suitable test instruments with the relevant previously determined test regions that are to be analyzed. In selecting the corresponding test instruments in the data processing program, all of the necessary properties that are relevant to the test instrument are automatically activated or retrieved and transferred later onto said instrument. This means that in an advantageous variant all of the eligible test instruments are stored in the data store. In accordance with the invention it is possible to preset the selected test instrument beforehand, meaning on the computer.

It should be appreciated here that, although the embodiments are related to the ultrasonic inspection technique, it is not intended that the invention be limited thereto. The apparatus of the invention could for example also be utilized with various X-ray devices or even with a combination of different methods such as X-ray and ultrasonic techniques.

The invention also makes it possible to establish a test plan beforehand using only one determined handheld test instrument, for example a self-sufficiently operated handheld test instrument that may be used with different probes and by means of which various test methods may be performed. This may be a reasonable choice when ultrasonic inspection is for example to be followed by surface hardness inspection with an eddy current inspection having to be carried out last. Accordingly, all the necessary settings may be carried out on the computer within the scope of the test plan. A test scheme may be established which the test operator merely needs to follow. This substantially facilitates work and inspection since the quite time-consuming in situ setting of the test instruments may be eliminated. Moreover, it is made certain that the input requirements are exactly met. This makes testing easier for inexperienced test operators in particular.

It is also possible to determine in advance the suitable way to visualize and evaluate the test values measured. This presents the advantage that standardized visualization and evaluation methods may be introduced, which in turn makes in situ inspection easier for the test operator by virtue of the presetting that has been made.

The apparatus of the invention can be utilized to particular advantage if a plurality of test objects of a kindred sort, such as for example pipeline tubes, are to be inspected. In such a case, a suited inspection scheme needs only be established once and may then be repeated as often as needed. The so to speak standardized measurement data obtained are easy and fast to compare.

In an advantageous developed implementation of the apparatus of the invention, it is also possible to already select further additional instruments during inspection planning. These instruments may be e.g., scanners or certain moving instruments such as inspection robots that may be pre-programmed.

The test values may be visualized both online and offline.

The inventors realized that certain elements or functions of instrument control software known hereto before may be used again and again, irrespective of the purpose of utilization for which a single instrument has been designed. These always reusable modules include e.g., operating parameters such as speech selection, voice selection, A-scan images, pressure parameters, access rights, instrument settings or result records. In prior art, purposeful selection of such individual elements forms the scope of functions of an instrument software. Generally, this selection is decided upon in the design phase of an instrument and widening or modifying this selection after the development phase is complete requires considerable effort and expense.

The standardized data processing program of the invention, by contrast, is conceived to have a modular structure. The planned overall scope of functions is thereby broken down into small and minute components that may be reassembled individually at a later stage. Exactly defined technical demands placed on these so-called plug-ins (=functional units) provide for smooth cooperation of all the individual parts. When, where and by whom an individual plugin is programmed is no longer important.

The possibility of combining the plugins, or rather the modular principle, is achieved by a "Common Application Architecture" (CAA) based on a "Universal Application Framework" (UAF).

Common Application Architecture is understood to refer to a modular system that is independent from the operating system. This modularity enables the user to divide the workspace on the screen in any number of panels of various sizes. Further, additional layers may at need be produced and also subdivided into any number of panels.

At any time, the user may select a number of panels and their specificity (height and width) to match the respective needs. As a result, the screen can be optimally made use of, irrespective of its resolution. Each panel may show any number of visualization surfaces (views) of a plugin.

Universal Application Framework is understood to refer to the programming instruction of the modular system (CAA). This makes certain that produced plugins be recognized as CAA-compatible software modules and be used by the CAA.

UAF further supports and contains the following functionalities:
automatic recognition and loading of plugins installed on the computer,
general communication and resource mechanism for plugins,
user administration with plugin-related access rights,
independent administration of the speech characteristics of the plugin,
the fact that one plugin may have a plurality of visualizing surfaces (views),
the possibility of positioning the views in the panels (selection, activation, moving function).

In complying with the programming instruction and the determined general scope of functions, it is made certain that extraneously developed plugins and also plugins that remain to be developed be CAA-compatible and are capable of cooperating together.

Advantageously, the software of the invention is based on a Windows principle which represents the plugins by certain symbols. Other operating systems rather than the Windows principle may also be utilized. A test scheme may be established by simply combining the symbols, said symbols being advantageously arranged in an easily understood surface structure. It is also possible that the user arranges and adjusts the surface structure according to needs. Hereto before, the A-scan in the instruments used was unmovably disposed on the left border of the screen; now, the software of the invention permits to move it to any position in the window.

Another major advantage is that the user will be given the ability to dynamically load and activate newly developed future plugins. What matters for the configuration is not the appearance of frame buttons or text fields but the structure of functions and groups of functions. This makes it possible to perfectly adapt future systems to their purpose of utilization, which last but not least also means ergonomic improvement to the user.

With the apparatus of the invention, even a relatively untrained user will be capable of establishing an inspection plan or an inspection scheme. He needs no detailed knowledge regarding the programming of such an inspection scheme and only needs to select the suited plugins.

In a particularly advantageous variant, the software is designed such that the user may "grab" the symbols or plugins with the mouse, using therefore a moving function for dragging these symbols into a window that is visible for this specific purpose (e.g., a drag and drop function). This moving function may be part of the "Common Application Architecture" (CAA), which is based on a "Universal Application Framework" (UAF).

Advantageously, it is possible to setup and connect plugins or symbols for other functions. Plugins with respect to user rights, DIN standards and the like may be envisaged here. Of course, improved or new test instruments may also advantageously be integrated. Then, it is only necessary to send the corresponding plugin to the user of the apparatus. This may occur by internet or by data carrier for example.

Accordingly, it is possible for the user to quickly and readily prepare a certain test instrument for a pending inspection using the apparatus of the invention on the one side and to thereby determine which test region is to be inspected by means of which test method and with which settings. If the tasks to be performed are more complicated, inspection planning may also include various test instruments, which is just as easy and simple to realize.

BRIEF DESCRIPTION OF THE DRAWINGS

Other advantages of the invention will become apparent from the following description of the Figures and from the claims.

DETAILED DESCRIPTION OF THE INVENTION

Figure 1:
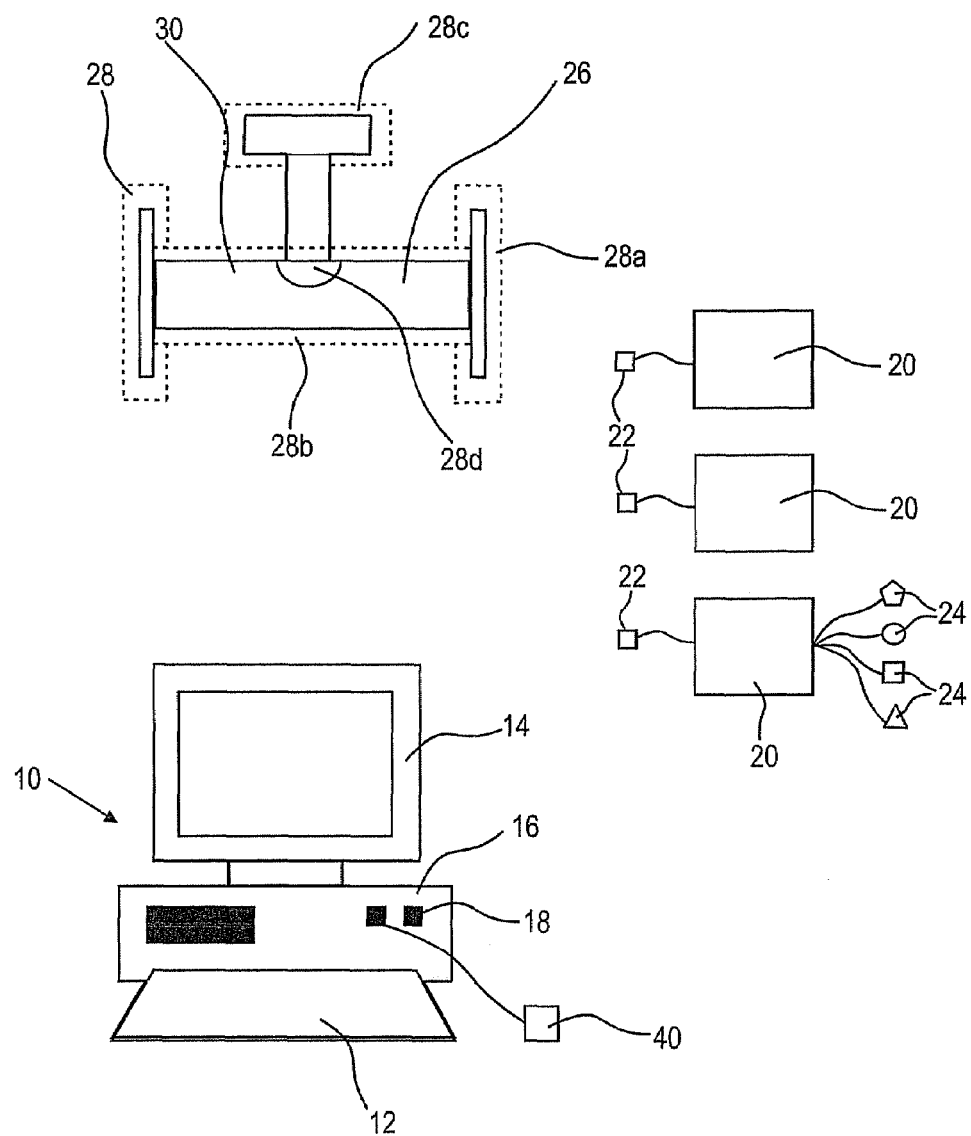
FIG. 1 shows a schematic diagram of the apparatus of the invention and an outlined test body.

FIG. 1 shows an apparatus 10 of the invention with an input device 12 (preferably a commercially available keyboard), an output device 14 (preferably a commercially available monitor), a data processing unit 16 (preferably a commercially available computer) comprising the connections or interfaces 18 for connecting the test instruments 20. Beside a usual PC, the use of a notebook or even of a handheld may be envisaged as long as they are capable of performing the necessary computing operations. The output instrument 14 must not necessarily have an imaging output display, in particular cases, numerical output may suffice.

Primarily, any suitable test instrument can be used as the test instrument 20 for performing non-destructive inspections. As already discussed, the reader is referred to ultrasonic test instruments by way of example. These instruments comprise a connection terminal 22 for connection to a data processing unit 16. It thereby only matters that the various test instruments 20 are connectable to the data processing unit 16 in such a manner that data can be transmitted in both directions. Wireless, for example Bluetooth, and wirebound connections are contemplated. Various probes 24, which in FIG. 1 are merely shown in the form of symbols, may be connected to the test instruments 20.

FIG. 1 further shows by way of example a test object 26 that is illustrated here in the form of a portion of a pipeline. Using the apparatus of the invention, it is now possible to input all the relevant data regarding the test object 26 into the data processing unit 16 or in a memory disposed therein. Then, various test regions 28, each of which is to be inspected with another test instrument 20 or probe 24, may be determined with the help of the apparatus 10. The test regions are shown by dashed lines. In the present exemplary embodiment, test regions 28a, 28b, 28c and 28d are provided. These various test regions are inspected with other ultrasonic test instruments. In test region 28b, the wall thickness may be tested, while in test region 28d, a weld seam 30 may be inspected. For each purpose, another test instrument 20 or probe 24 is to be utilized.

All the necessary data regarding the test instruments 20, the probes 24, the test object 26 and possibly other instruments that have not been illustrated herein are filed in the data processing unit 16 or may be input therein so that a corresponding inspection scheme may be established. As a result, it is possible to completely prepare the entire inspection of the test object 26 using the apparatus of the invention and to include different test instruments 20 in the planning.

Figure 2:
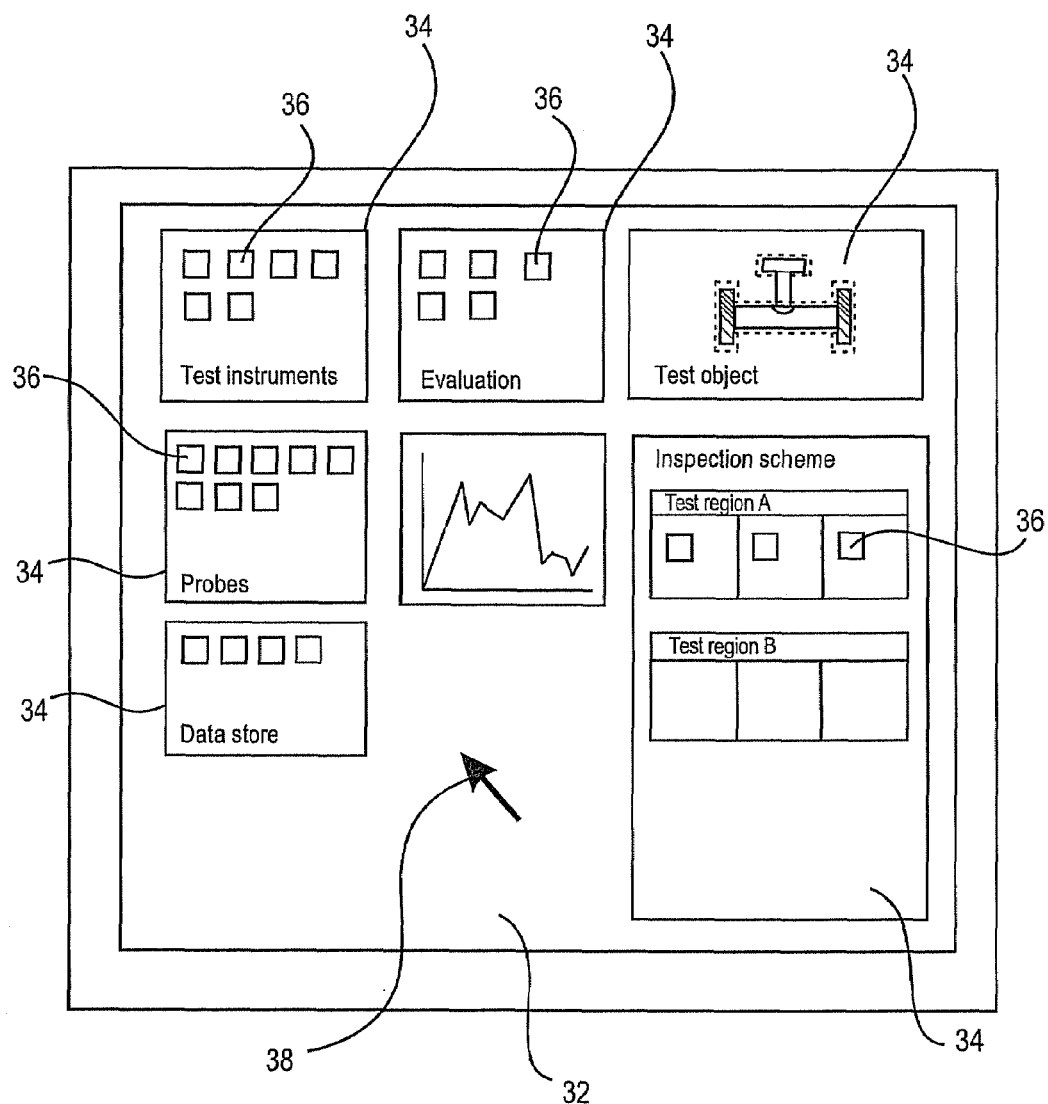
FIG. 2 shows a schematic diagram of a user interface of the invention as it may be represented on an output device.

FIG. 2 illustrates how a user interface 32 of the invention, which is provided through the output device 14, may be represented. The user interface 32 is advantageously divided into various windows 34 that may be freely arranged and distributed in the fashion of the known Windows-system. Inside the windows 34 there are located the functional units or plugins 36, each representing different test instruments 20, different evaluation possibilities, different probes 24, different possibilities of data storage and so on. The plugins 36 are linked to the associated and necessary data. The test object 26 may also be represented in a window 34, a three-dimensional representation being preferred for being particularly suitable. There is further provided a mouse pointer 37 for control by a mouse 40 or a similar input device such as a touchpad.

There is further provided a window 34 in which the inspection scheme to be planned can be compiled. For this purpose, it is advantageously possible to "grab" the discrete plugins 26 with the mouse pointer 38 and to drag them into the corresponding windows 34 of the inspection scheme. This makes simple and fast association of the diverse test regions 28, which are represented each by a window 34 of their own, with corresponding test instruments, evaluation methods, probes or data stores possible. It is further possible to determine the test sequence in the inspection scheme. Ideally, a test operator would then merely start the inspection scheme on the site, then connect the test instrument 20 required or connect it to the probe 24 requested and then carry out the inspection of a certain test region 28. He needs not care for possible evaluation possibilities or the like since these parameters have already been set. Once inspection of this test region 28 is complete, the test operator will be automatically invited to connect another test instrument 20 or another probe 24 to inspect another test region 28. It is also possible not to exchange the test instrument, with other parameters, such as the type of evaluation for example, however changing automatically when the next test region 28 is being inspected.

On the user interface 32, evaluation images such as an A-scan or a B-scan or wall thicknesses or the like may also be represented directly.

There may also be provided a window 34 with plugins 36 that contains other peripherals that might be needed for a certain test and that also need to be preset.

Using the modular system shown, the user is given the possibility to freely design its user interface 32 and to thus always work with the same user interface. He needs to adapt to a certain user interface 32 depending on the test instrument 20. The functions included in a program or system, the location of this function and the possibilities of using them may be determined anew any time, whenever the need arises, even during operation.

The procedure of planning an inspection using the apparatus 10 of the invention is for example as follows:
1. Selecting or determining the test object 26,
2. Determining the relevant test regions 28,
3. Selecting suitable test instruments 20 or probes 24 for the selected test regions 28,
4. Selecting the type of visualization and evaluation of the test values of a respective one of the test instruments 20 or as a function of the test regions,
5. Selecting and fixing the manner of storing and archiving data.

The sequence of the inspection may also be determined. It is also possible to change the evaluation and visualization of the test data during inspection. It may however also be judicious to precisely fix this. Selection of the various test instruments 20, of the probes 24, of the kind of visualization and evaluation and of the kind of storage and archiving is easy and fast to perform using the moving function with the help of the mouse pointer 38, by dragging the corresponding plugins 36 into the corresponding windows 34.

The invention claimed is:

1. An apparatus for planning preparing, performing and evaluating a non-destructive inspection of a test object having various test regions, wherein at least some of the test regions require different suitable test instruments for testing the test regions, said apparatus having one or more discretionary suitable test instruments and comprising:
   an input device,
   an output device,
   a data store,
   a data processing unit,
   an interface for connecting a respective one of the test instruments through which data are adapted to be transmitted in both directions,
   a standardized data processing program for defining a test object by data input or selecting it from the data store, determining various test regions of a test object, selecting at least one determined test instrument from a group of test instruments for each of the test regions requiring different suitable test instruments and associating each with a respective one of the test regions, with all relevant properties of the test instrument being stored in the data store,
   carrying out test-relevant settings for the selected instrument,
   selecting a kind of visualization and evaluation of measured test values,
   archiving and storing test results obtained,
   establishing a test scheme, with all predetermined settings being transferred to the respective test instrument upon connection thereof so that it is preset for inspection.

2. The apparatus as set forth in claim 1, wherein additional instruments are selectable through the standardized data processing program and may be associated.

3. The apparatus as set forth in claim 1, wherein all the selectable data are represented by standardized plugins that may be combined together by virtue of a standardized interface.

4. The apparatus as set forth in claim 3, wherein the possibility of combining the plugins, or rather the modular structure, is given by a "Common Application Architecture" (CAA) which is based on a "Universal Application Framework" (UAF).

5. The apparatus as set forth in claim 4, wherein visualization and evaluation of the test values obtained may occur both online and offline.

6. The apparatus as set forth in claim 5, wherein a user interface, which is configured in the fashion of a Windows interface and in which the test scheme may be established, based on the plugins, is disposed on the output device.

7. The apparatus as set forth in claim 6, wherein the plugins are selectable with the help of a moving function and may be associated.

8. The apparatus as set forth in claim 1, wherein the test instruments are implemented to be ultrasonic test instruments.

9. A method for carrying out a non-destructive inspection, the method comprising:
   providing an apparatus for planning preparing, performing and evaluating a non-destructive inspection of a test object having various test regions, wherein at least some of the test regions require different suitable test instruments for testing the test regions, said apparatus having one or more discretionary suitable test instruments and an input device, an output device, a data store, a data processing unit, an interface for connecting a respective one of the test instruments through which data are adapted to be transmitted in both directions, and a standardized data processing program;
   inputting or selecting relevant data of a test object,
   determining test regions,
   selecting test instruments or probes suited for the test regions,
   selecting a manner of visualizing and evaluating measured test values,
   selecting a manner of storing and archiving the test results;
   establishing an inspection scheme in predetermined settings with respective test instruments thereof to be used for determining the non-destructive inspection.

10. The method as set forth in claim 9, wherein an inspection scheme can be established in which the order in which the respective test instruments or probes are used for inspection can be fixed.

11. The method as set forth in claim 9, wherein further additional instruments are selected.

* * * * *